United States Patent [19]

Westernacher et al.

[11] Patent Number: 4,847,440
[45] Date of Patent: Jul. 11, 1989

[54] METHOD OF MANUFACTURING PROPYNOL

[75] Inventors: Helmut Westernacher, Haltern; Karl Aertken, Duelmen; Thomas Stieren, Haltern, all of Fed. Rep. of Germany

[73] Assignee: Huels Aktiengesellschaft, Marl, Fed. Rep. of Germany

[21] Appl. No.: 236,189

[22] Filed: Aug. 25, 1988

[30] Foreign Application Priority Data

Sep. 4, 1987 [DE] Fed. Rep. of Germany ....... 3729678

[51] Int. Cl.$^4$ ..................... C07C 29/42; C07C 33/042
[52] U.S. Cl. ..................................... 568/874; 568/855
[58] Field of Search ......................................... 568/874

[56] References Cited

U.S. PATENT DOCUMENTS

| | | | |
|---|---|---|---|
| 2,345,170 | 3/1944 | Zeltner et al. | 568/874 |
| 2,385,546 | 9/1945 | Smith | 568/874 |
| 2,712,560 | 7/1955 | McKinley et al. | 568/874 |

FOREIGN PATENT DOCUMENTS

| | | | |
|---|---|---|---|
| 1174765 | 7/1964 | Fed. Rep. of Germany | 568/874 |
| 1284964 | 12/1968 | Fed. Rep. of Germany | 568/874 |
| 1232257 | 5/1971 | United Kingdom | 568/874 |

Primary Examiner—J. E. Evans
Attorney, Agent, or Firm—Oblon, Spivak, McClelland, Maier & Neustadt

[57] ABSTRACT

A process for manufacturing propynol from formaldehyde and acetylene is disclosed. In this process the acetylene is first dissolved in a dimethoxymethane solvent under strong cooling and at slight gauge pressure. The cool acetylene-containing solution is then fed to a reactor charged with formaldehyde and a catalyst.

8 Claims, 1 Drawing Sheet

METHOD OF MANUFACTURING PROPYNOL

BACKGROUND OF THE INVENTION

1. Field of the Invention

The invention relates to processes for manufacturing propynol from acetylene and formaldehyde.

2. Discussion of the Background

Propynol is used for synthesizing polyacetylenes and other natural substances. It is also used as a corrosion protection agent in the electroplating industry.

Propynol is produced in small amounts as a by-product in the production of 1,4-butynediol from formaldehyde and acetylene.

In the known processes for producing propynol, the starting materials are also formaldehyde and acetylene. In these processes the reaction of propynol with formaldehyde to form 1,4-butynediol is suppressed by the use of special reaction conditions. For example, German Pat. No. 1,174,765 discloses the use of N-methylpyrrolidone, which is a good solvent for acetylene and therefore enables a high acetylene concentration.

The reaction of acetylene and formaldehyde in the presence of copper acetylide leads principally to propynol, according to German Pat. No. 1,174,765. Separation out of the high boiling solvent however is technically complex and cost-intensive.

According to German Pat. No. 1,284,964, acetylene and formaldehyde can be reacted, with the aid of copper acetylide on a support, to form 1,4-butynediol and propynol. The two products are formed in comparable amounts. Formaldehyde dimethylacetal is noted as a solvent, but the preferred solvent is said to be butyrolactone. The dissolution is carried out under cooling, but requires increasingly high pressures, which represent a major safety risk.

The underlying problem in the production of propynol is the absence of a process permitting the production of propynol from acetylene and formaldehyde at decreased cost and with increased process safety.

SUMMARY OF THE INVENTION

Accordingly, it is an object of this invention to provide a process for the preparation of propynol from acetylene and formaldehyde.

It is another object of this invention to provide a process for the economical production of propynol from acetylene and formaldehyde.

It is another object of this invention to provide a safe process for the production of propynol from acetylene and formaldehyde.

The inventors have now discovered a process which satisfies all of the above objects of this invention and other objects which will become apparent from the description of the invention given hereinbelow. In the present process for manufacturing propynol from acetylene and formaldehyde, dimethoxymethane and a copper acetylide catalyst are used. The acetylene is dissolved in the dimethoxymethane under strong cooling, either at normal pressure or under a slight gauge pressure, and this cooled solution is then introduced into the reactor.

BRIEF DESCRIPTION OF THE DRAWINGS

A more complete appreciation of this invention and many of its attendant advantages will be readily obtained as the same becomes better understood by reference to the following description when considered in connection with the accompanying drawing, wherein.

DETAILED DESCRIPTION OF THE PREFERRED EMBODIMENTS

Figure 1:
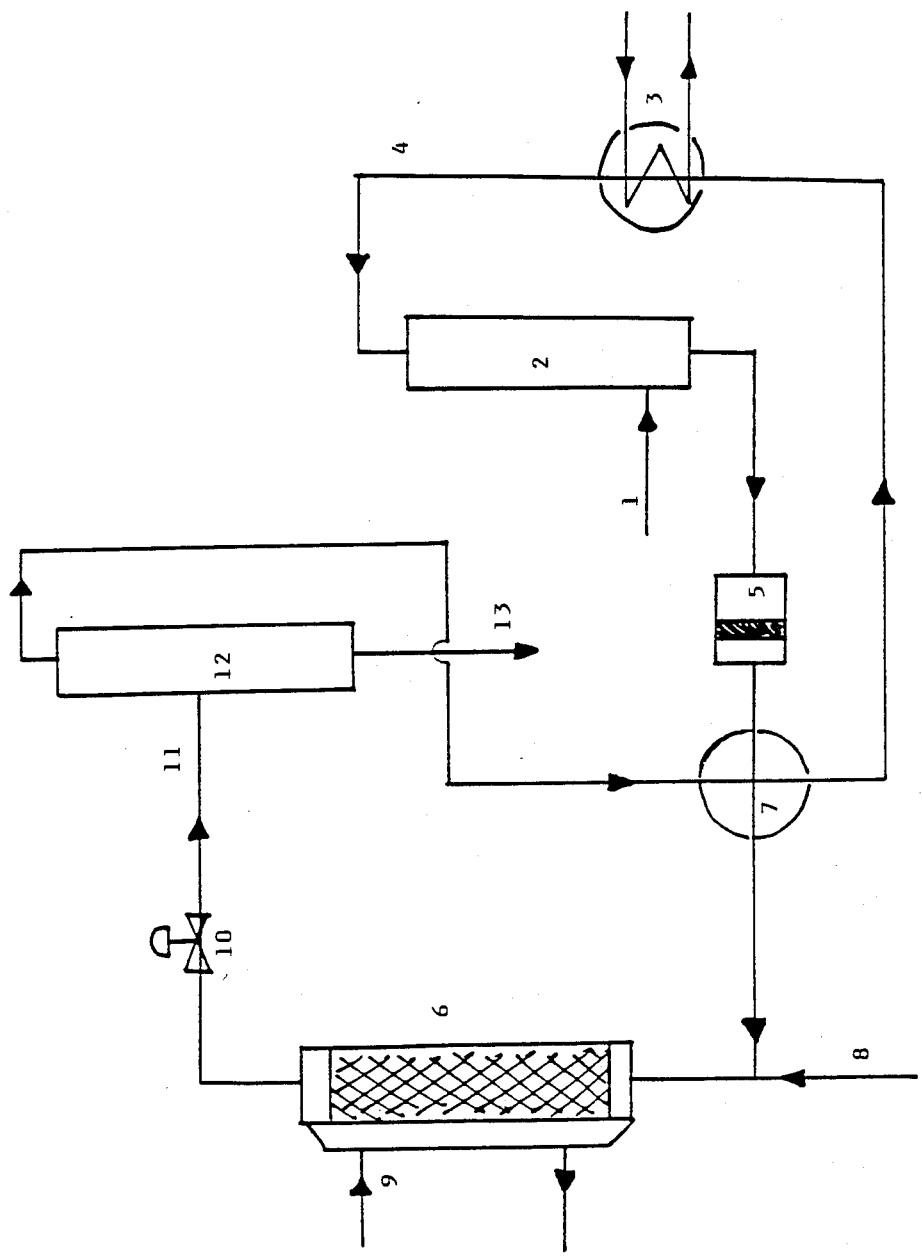
FIG. 1 provides a schematic illustration of an installation in which the present process can be performed.

In the present invention acetylene is dissolved in dimethoxymethane under strong cooling, at normal pressure or slight gauge pressure, and the cooled solution is fed to the reactor.

The dissolution of acetylene in dimethoxymethane can be carried out, e.g., in an absorber, in which temperatures of $-10°$ to $-50°$ C. are maintained, preferably $-15°$ to $-40°$ C., and pressures of from 1 to 5 bar, preferably 1.5 to 4 bar, are used.

According to the invention the acetylene can be supplied to the reaction at low pressure. The method is therefore simple and safe in operation. Further, it enables large scale-up with decreased hazard.

General Description of the Method

As illustrated in FIG. 1, in the present invention as it is illustrated in the figure acetylene is passed through line 1 into absorber 2. A vessel with stirrer may be used as the absorber, or an absorption column filled with packing may be used. The acetylene can be fed concurrently with or countercurrently to the solvent.

The solvent, dimethoxymethane, which may also contain up to 20% (vol.) methanol, but preferably contains <10% (vol.) methanol, is cooled in a heat exchanger 3 and passed into the absorber via line 4.

A solution saturated with acetylene (depending on pressure and temperature) is pumped into the reactor 6 by pump 5. For improved energy utilization, heat exchange is carried out in a heat exchanger 7 operating between the acetylene solution and the dimethoxymethane being recycled. The required amount of formaldehyde is fed through line 8. Aqueous formaldehyde solutions with formaldehyde contents of 30 to 80% are used. Also, formaldehyde solutions in dimethoxymethane may be used.

The reactor is filled with a catalyst packing (fixed bed). The catalyst is copper acetylide, which may be in the forms described in, e.g., German Pat. Nos. 1,235,295 and 1,013,279. The reactor is equipped with cooling and heating means 9. The reactor is filled hydraulically. The reaction pressure is maintained at 10 to 200 bar by a pressure regulation device 10. The reaction temperature is 85° to 150° C.

The reaction mixture, which essentially is comprised of dimethoxymethane, methanol, propynol, 1,4-butynediol, formaldehyde, and water, is passed through line 11 into the dimethoxymethane recovery column 12. The dimethoxymethane/methanol mixture which is separated out is recycled to the process. The mixture of propynol, 1,4-butynediol, formaldehyde, and water is passed to the standard refining steps, via line 13.

Other features of this invention will become apparent in the course of the following descriptions of exemplary embodiments which are given for illustration of the invention and are not intended to be limiting thereof.

Example

Catalyst (comprised of ⅛ inch pellets) (500 ml) was charged into a tubular reactor (length 1000 mm, inner diameter 23 mm) equipped with temperature and pressure measuring devices and a jacket for heating and cooling. The catalyst was prepared as described in German Pat. No. 1,235,295, and contained 35% Cu, 3% Bi$_2$O$_3$, and 43% magnesium silicate.

Acetylene and dimethoxymethane were introduced into a stirred autoclave at $-16°$ C. and 2.1 bar, to produce a saturated solution of acetylene in dimethoxymethane.

This saturated solution was continuously fed to the reactor by a piston pump, at 444 g/hr. 56 g/hr of a 50% aqueous formaldehyde solution was added in measured amounts to the said saturated solution which was heated to the reaction temperature of 115° C. A second piston pump was used for the formaldehyde addition.

The heat of reaction which was liberated was removed by cooling. The reaction pressure was 20 bar. The mean residence time of the reaction mixture in the reactor was 0.7 hr. The material withdrawn from the reactor had the following composition:

Dimethoxymethane: 75.1%
Methanol: 6.9%
1,4-Butynediol: 6.3%
Water: 6.3%
Propynol: 5.1%
Formaldehyde: 0.3%

From 500 g/hr reaction mixture, dimethoxymethane and methanol were separated out and recovered. The remainder was processed by distillation according to German Pat. No. 1,002,324. The propynol product was >99% pure.

Obviously, numerous modifications and variations of the present invention are possible in light of the above teachings. It is therefore to be understood that within the scope of the appended claims, the invention may be practiced otherwise than as specifically described herein.

What is new and desired to be claimed by Letters Patent of the United States is:

1. A process for the production of propynol from acetylene and formaldehyde, comprising:
    (i) dissolving acetylene in a dimethoxymethane solvent at a temperature of from $-10°$ C. to $-50°$ C.;
    (ii) combining in a reactor (iia) a copper acetylide catalyst, (iib) formaldehyde, and (iic) said acetylene dissolved in the dimethyxomethane solvent; and
    (iii) obtaining propynol.

2. The process of claim 1, wherein said acetylene is dissolved in the dimethoxymethane solvent under a pressure from 1 to 5 bar.

3. The process of claim 1, wherein said acetylene is dissolved in the dimethoxymethane solvent at a temperature of from $-15°$ C. to $-40°$ C.

4. The process of claim 1, wherein said acetylene is dissolved in the dimethoxymethane solvent under a pressure of from 1.5 to 4 bar.

5. The process of claim 1, wherein said dimethoxymethane solvent contains methanol in an amount of up to 20 vol. %.

6. The process of claim 1, wherein said dimethoxymethane solvent contains methanol in an amount of less than 10 vol. %.

7. The process of claim 2, wherein said acetylene is dissolved in the dimethoxymethane solvent at a temperature of from $-15°$ C. to $-40°$ C.

8. The process of claim 3, wherein said acetylene is dissolved in the dimethoxymethane solvent under a pressure of from 1.5 to 4 bar.

* * * * *

UNITED STATES PATENT AND TRADEMARK OFFICE
CERTIFICATE OF CORRECTION

PATENT NO. : 4,847,440

DATED : July 11, 1989

INVENTOR(S) : HELMUT WESTERNACHER

It is certified that error appears in the above-identified patent and that said Letters Patent is hereby corrected as shown below:

Column 4, line 11, please delete "dimethyxomethane" and insert --dimethoxymethane--.

Signed and Sealed this

Twenty-third Day of October, 1990

Attest:

HARRY F. MANBECK, JR.

*Attesting Officer*     *Commissioner of Patents and Trademarks*